(12) United States Patent
Qasem et al.

(10) Patent No.: US 7,897,172 B2
(45) Date of Patent: Mar. 1, 2011

(54) TABLETS EXHIBITING REDUCED DRUG RELEASE VARIABILITY

(75) Inventors: Jaber G. Qasem, Portage, MI (US); Sumner H. Cathcart, Mattawan, MI (US); Jack T. Irwin, Kalamazoo, MI (US)

(73) Assignee: L. Perrigo Company, Allegan, MI (US)

( * ) Notice: Subject to any disclaimer, the term of this patent is extended or adjusted under 35 U.S.C. 154(b) by 2136 days.

(21) Appl. No.: 10/848,447

(22) Filed: May 18, 2004

(65) Prior Publication Data

US 2005/0260267 A1    Nov. 24, 2005

(51) Int. Cl.
  *A61K 9/20*   (2006.01)
  *A61K 9/22*   (2006.01)
  *A61K 9/36*   (2006.01)
  *A61K 9/14*   (2006.01)
  *A61K 31/04*  (2006.01)
  *A01N 33/18*  (2006.01)

(52) U.S. Cl. .......... 424/464; 424/465; 424/468; 424/480; 424/488; 514/741

(58) Field of Classification Search ................. 424/464, 424/465, 468, 480, 488
See application file for complete search history.

(56) References Cited

U.S. PATENT DOCUMENTS

| | | | |
|---|---|---|---|
| 4,814,181 A | 3/1989 | Jordan et al. | |
| 4,820,522 A | 4/1989 | Radebaugh et al. | |
| 4,946,685 A * | 8/1990 | Edgren et al. | 424/472 |
| 4,968,509 A * | 11/1990 | Radebaugh et al. | 424/470 |
| 5,004,613 A | 4/1991 | Radebaugh et al. | |
| 5,009,895 A | 4/1991 | Lui | |
| 5,073,380 A | 12/1991 | Babu et al. | |
| 5,283,065 A | 2/1994 | Doyon et al. | |
| 5,773,031 A * | 6/1998 | Shah et al. | 424/497 |
| 5,895,663 A | 4/1999 | Irwin et al. | |
| 5,900,425 A * | 5/1999 | Kanikanti et al. | 514/356 |
| 5,945,123 A | 8/1999 | Hermelin | |
| 6,177,102 B1 | 1/2001 | Chen et al. | |
| 6,699,502 B1 | 3/2004 | Fanara et al. | |

* cited by examiner

*Primary Examiner* — Mina Haghighatian
*Assistant Examiner* — Mei-Ping Chui
(74) *Attorney, Agent, or Firm* — Price, Heneveld, Cooper, DeWitt & Litton, LLP

(57) ABSTRACT

A compressible extended release tablet or tablet layer having a drug release profile that is not strongly dependent on tablet hardness may be prepared by dry blending a pharmaceutically active ingredient with hydroxypropyl methylcellulose, wherein the hydroxypropyl methylcellulose has a bimodal or multimodal number average molecular weight distribution that includes at least one mode over 20,000 Daltons and at least one mode under 10,000 Daltons. An additional advantage of the invention is that the tablet formulations may be prepared without resort to wet granulation.

6 Claims, 1 Drawing Sheet

TABLETS EXHIBITING REDUCED DRUG RELEASE VARIABILITY

FIELD OF THE INVENTION

This invention pertains to pharmaceutical tablets and particularly to compressed tablets exhibiting extended release properties.

BACKGROUND OF THE INVENTION

As is evident from a review of the relevant patent, scientific and industrial literature, consistently achieving a desired extended drug release profile can be rather difficult. Factors that can influence the extended release profile of a tablet include the physical and chemical characteristics of the pharmaceutically active ingredient, patient-to-patient variability in the physiological environment in which the drug is released, variability in the temporal physiological environment in the which the drug is released for an individual patient, the nature of the inactive ingredient selected for preparing the tablet, and the manner in which the ingredients are processed and combined to prepare the tablet.

Even the amount of pressure used during tablet compression can influence tablet hardness, which can in turn have a profound effect on the drug release profile. Accordingly, once an effective tablet preparation procedure has been established for achieving a desired extended drug release profile for a particular pharmaceutically active ingredient, great care is normally taken to ensure that the procedure is precisely duplicated for each production run to avoid variation in the drug release profile due to variations in the properties of the tablet.

It would be desirable to eliminate, or at least reduce, the effect of tablet hardness on drug release rate, such as to facilitate production of different types of tablets from the same or similar formulation. For example, if the effects of tablet hardness on the drug release profile could be eliminated or significantly reduced, it may be possible to prepare, from identical or very similar formulations, chewable and swallowable tablets having different hardnesses, but the same or very similar drug release profiles. Eliminating or substantially reducing the effect of tablet hardness on drug release profile is also beneficial for production of a single tablet type, since it reduces the potential for variation in the release profile from one production batch to another.

SUMMARY OF THE INVENTION

The invention is directed to pharmaceutical tablets and a process for preparing pharmaceutical tablets, which utilize an inactive ingredient that reduces the variability of extended drug release profiles. More specifically, the invention is directed to the use of hydroxypropyl methylcellulose (HPMC) having a bimodal or multimodal number average molecular weight distribution to reduce or eliminate the effect of tablet hardness on extended drug release profiles.

These and other features, advantages and objects of the present invention will be further understood and appreciated by those skilled in the art by reference to the following specification and claims.

DESCRIPTION OF THE PREFERRED EMBODIMENTS

Figure 1:
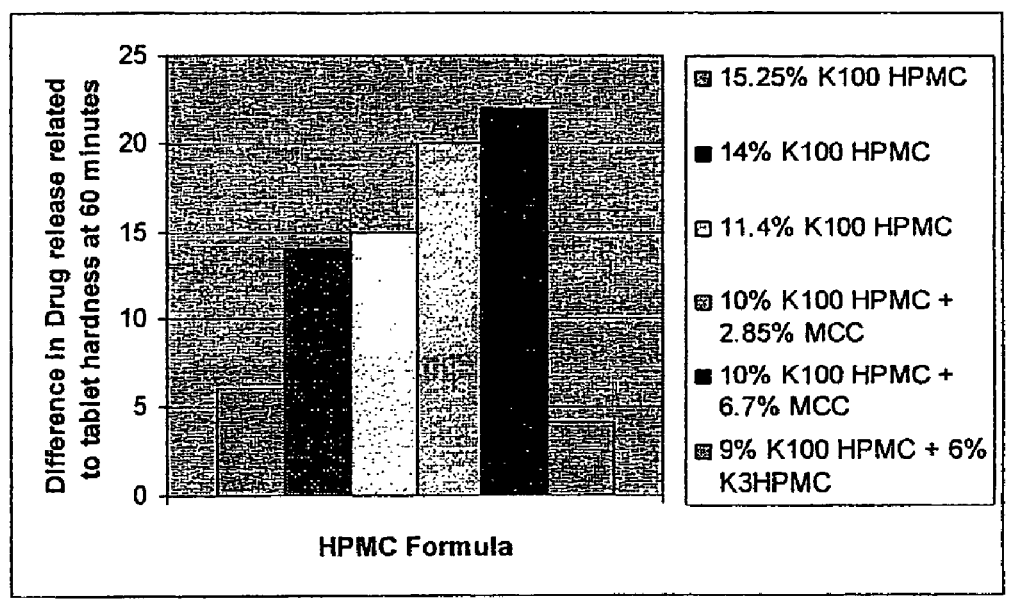
FIG. 1 is a correlation of drug release variability (dissolution) associated with tablet hardness at 60 minutes for different HPMC formulations.

The tablets in accordance with this invention include a pharmaceutically active ingredient and HPMC having a bimodal or multimodal number average molecular weight distribution. The number average molecular weight distribution can be determined using various conventional techniques, such as gel chromatography, to determine the number of HPMC molecules (e.g., moles) of any given molecular weight in a sample. The number average molecular weight distribution may be represented graphically by plotting the number (e.g., moles) of HPMC molecules of a given molecular weight as a function of the molecular weight. A HPMC sample having a bimodal number average molecular weight distribution will have two distinct peaks in a number average molecular weight distribution graph. Distinct peaks are peaks (or modes) which have essentially no overlapping areas. Stated differently, there are not any appreciable (e.g., detectable) amounts of molecules having a molecular weight between the peaks. A multimodal number average molecular weight distribution has at least three distinct peaks.

The extended release tablets and extended release tablet layers may comprise a pharmaceutically active ingredient in a therapeutically effective amount, a hydroxypropyl methylcellulose having a number average molecule weight over 20,000, and a hydroxypropyl methylcellulose having a number average molecular weight less than 10,000. In another aspect, the extended release tablet or layer may consist essentially of a therapeutically effective amount of a pharmaceutically active ingredient, a hydroxypropyl methylcellulose having a number average molecular weight more than 20,000, and a hydroxypropyl methylcellulose having a number average molecular weight less than 10,000. Such tablet or layer that is "consisting essentially of" an active ingredient, a high molecular weight hydroxypropyl methylcellulose and a low molecular weight hydroxypropyl methylcellulose is intended to exclude other ingredients that have a very substantial effect on the drug release rate.

The invention has been exemplified herein by tablets comprising acetaminophen as the active ingredient. However, the invention is not limited to acetaminophen tablets. Generally, any pharmaceutically active material that can be combined with HPMC, and optionally other ingredients, and can be compressed into a tablet may be employed. Suitable pharmaceutically active materials are generally any solid material, including crystalline materials, amorphous solids, powdered materials, etc.

Non-limiting examples of pharmaceutically active ingredients that may be advantageously employed in the tablets and processes of this invention include analgesics, anorexics, antihelmintics, antibacterials, anticonvulsants, antifungals, antidepressants, antibiotics, antihistamines, antiulcer drugs, antihypertensives, bronchodilators, immunosuppressants, adrenergics, muscle relaxants, muscle contractants, diuretics, hypnotics and histamine $H_2$ antagonists.

A preferred method of preparing the HPMC having a bimodal or multimodal number average molecular weight distribution involves combining at least two commonly available HPMC products which each have a monomodal number average molecular weight distribution. For example, METHOCEL® K100 LV PREM CR (commercially available from The Dow Chemical Company, Midland, Mich.), which has a number average molecular weight of about 28,800, may be combined with METHOCEL® K3 PREM LV (also available from The Dow Chemical Company), which has a number average molecular weight of about 6,500, to obtain a HPMC blend having a bimodal molecular weight distribution, with one mode at about 28,800 Daltons and second mode at about 6,500 Daltons.

In accordance with the principles of this invention, the HPMC has at least a bimodal number average molecular weight distribution, with at least one mode greater than 20,000 Daltons, and at least one other mode less than 10,000 Daltons. It has been discovered that this combination may be utilized to prepare pharmaceutical tablets having extended drug release properties that have a very low dependency on tablet hardness, allowing greater flexibility in the production process and preparation of different tablets, such as swallowable and chewable tablets, having similar or substantially the same drug release profile. A suitable amount of lower molecular weight (e.g., less than 10,000 Daltons) hydroxypropyl methylcellulose is from about 1% to about 10% of the total tablet formulation weight, and more typically from about 4% to about 8%. A suitable amount of higher molecular weight (e.g., greater than 20,000 Daltons) hydroxypropyl methylcellulose is also from about 1% to about 10% of the total tablet formulation weight, and more typically from about 4% to about 10%.

For purposes of the invention, a blend of a higher molecular weight HPMC and a lower molecular weight HPMC results in and is equivalent to hydroxypropyl methylcellulose having a bimodal molecular weight distribution.

An additional advantage of the invention is that a predictable drug release rate may be achieved that is relatively independent of tablet hardness in a tablet that comprises a high level of drug (i.e., high drug loading). Typically, relatively low amounts of ingredients other than the active and the hydroxypropyl methylcellulose may be employed. For example, the compositions in accordance with this invention may typically contain from about 70% to about 95% of a pharmaceutically active ingredient, and may typically include inactive ingredients other than HPMC in an amount of less than 10%. Thus, the compositions of this invention may comprise, consist essentially of, or consist of a pharmaceutically active ingredient, and hydroxypropyl methylcellulose having a bimodal and multimodal number average molecular weight distribution that includes a HPMC having a number average molecular weight over 20,000 Daltons and a HPMC having a number average molecular weight under 10,000 Daltons.

Other inactive ingredients that may optionally be employed in relatively small quantities, and which do not affect the fundamental and essential characteristics of the invention include lubricants, such as magnesium stearate, flow agents such as silicon dioxide, and binders that facilitate compression, such as microcrystalline cellulose. A lubricant such as magnesium stearate may be added in an amount from about 0.1% to about 1.0% by weight, a binder such as microcrystalline cellulose may be added in an amount from about 2.5% to about 5.0% by weight, and a flow agent such as silicon dioxide may be added in an amount from about 0.5% to about 1% by weight. The tablets may also contain relatively minor amounts of other conventional tablet excipients and/or adjuvants, such as flavorants, sweeteners, colorants, etc. Such ingredients are preferably present in a relatively minor amount, such as about 1% or less.

Preferably, the tablet ingredients are dry blended and compressed in a tablet press.

In accordance with certain embodiments of the invention, a bilayer tablet having an extended release layer and an immediate release layer is provided. The extended release layer includes the active ingredient, hydroxypropyl methylcellulose, and optional excipients and/or adjuvants as described above. A suitable immediate release layer may be prepared by combining the active with a lubricant, and one or more disintegrating agents. Binders and other excipients and/or adjuvants may be included in the immediate release layer if necessary or desired. The immediate release layer may be compressed directly on a previously compressed extended release layer, or alternatively, the extended release layer may be compressed onto a previously compressed immediate release layer. Typically, the extended release layer contains from about 35% to about 65% of the total weight of the pharmaceutically active ingredient, and more desirably from about 40% to about 60%, with the balance of the pharmaceutically active ingredient being present in the immediate release layer. The active ingredient in the immediate release layer may be the same or different from the active ingredient in the extended release layer.

The principles of the invention are further illustrated by the following non-limiting examples.

EXAMPLES

In a first example, a bilayer acetaminophen tablet is prepared using the following ingredients:

| MATERIAL | % | AMT (GM) |
|---|---|---|
| LAYER #1 | | |
| COMPAP WSE 95% (95% Acetaminophen) | 80.33 | 9640.0 |
| METHOCEL ® K100L V PREM CR | 8.91 | 1070.0 |
| Colloidal Silicon Dioxide | 0.78 | 90.0 |
| METHOCEL ® K3 PREM L V | 6.09 | 730.0 |
| Microcrystalline Cellulose | 3.50 | 420.0 |
| MAGNESIUM STEARATE | 0.39 | 50.0 |
|  | 100.0 | 12000.0 |
| LAYER #2 | | |
| APAP 90% (90% Acetaminophen) | 100.0 | 8661.2 |
|  | 100.0 | 8661.2 |

The total tablet weight is about 792.0 milligrams, with about 650 milligrams of acetaminophen per tablet. Layer 1 has a total weight of about 430.0 milligrams (351.0 milligrams acetaminophen), and Layer 2 has a total weight of about 332.0 milligrams (about 298.8 milligrams acetaminophen). The mixtures for each of the layers are prepared and the layers are sequentially compressed on a Manesty Rotopress MK II. The resulting tablets have a hardness from about 18.7 SCU to about 28.4 SCU. During dissolution testing, using a 0.1 N hydrochloric acid at pH 1.2, it is found that from about 47 to about 51% of the acetaminophen is released in 15 minutes, from about 60 to about 64% in about 60 minutes, and from about 81 to about 83% of the acetaminophen is released in 180 minutes.

In another example, a bilayer acetaminophen tablet is prepared using the following ingredients:

| MATERIAL | % | AMT (GM) |
|---|---|---|
| LAYER #1 | | |
| COMPAP WSE 95% (95% Acetaminophen) | 80.33 | 9640.0 |
| METHOCEL ® K100L V PREM CR | 8.91 | 1070.0 |
| Colloidal Silicon Dioxide | 0.78 | 90.0 |

-continued

| MATERIAL | % | AMT (GM) |
|---|---|---|
| METHOCEL ® K3 PREM L V | 6.09 | 730.0 |
| Microcrystalline Cellulose | 3.50 | 420.0 |
| MAGNESIUM STEARATE | 0.39 | 50.0 |
| | 100.0 | 12000.0 |
| LAYER #2 | | |
| APAP 90% (90% Acetaminophen) | 100.0 | 10590.4 |
| | 100.0 | 10590.4 |

The total tablet weight is about 785.7 milligrams, with about 650 milligrams of acetaminophen per tablet. Layer 1 has a total weight of about 417.4 milligrams (318.5 milligrams acetaminophen), and Layer 2 has a total weight of about 368.3 milligrams (about 331.5 milligrams acetaminophen). The mixtures for each of the layers are prepared and the tablet layers are sequentially compressed on a Manesty Rotopress MK II. The resulting tablets have a hardness from about 16.3 SCU to about 26.9 SCU. During dissolution testing, using a 0.1 N hydrochloric acid at pH 1.2, it is found that from about 52 to about 55% of the acetaminophen is released in 15 minutes, from about 66 to about 68% in about 60 minutes, and from about 85 to about 88% of the acetaminophen is released in 180 minutes.

TABLE 1

Association of drug release with Tablet hardness at different (METHOCEL ® K100L V PREM CR) percentages.

| % HPMC (K100) | Drug/Polymer Ratio | Hardness (SCU) | Time (min) | % Drug Release (D.R.) | Difference in % D.R. |
|---|---|---|---|---|---|
| 15.2 | 5.1 | 17.1 | 15 | 51 | At 15 min = 5 |
| | | | 60 | 63 | |
| | | | 180 | 79 | At 60 min = 6 |
| | | 29.6 | 15 | 46 | |
| | | | 60 | 57 | At 180 min = 25 |
| | | | 180 | 74 | |
| 14 | 5.6 | 17.8 | 15 | 53 | At 15 min = 17 |
| | | | 60 | 66 | |
| | | | 180 | 81 | At 60 min = 14 |
| | | 29.8 | 15 | 36 | |
| | | | 60 | 52 | At 180 min = 11 |
| | | | 180 | 70 | |
| 11.4 | 7.4 | 12.8 | 15 | 60 | At 15 min = 14 |
| | | | 60 | 77 | |
| | | | 180 | 91 | At 60 min = 15 |
| | | 24.4 | 15 | 46 | |
| | | | 60 | 62 | At 180 min = 8 |
| | | | 180 | 83 | |
| 10 | 8.6 | 13 | 15 | 68 | At 15 min = 19 |
| | | | 60 | 85 | |
| | | | 180 | 96 | At 60 min = 20 |
| | | 24 | 15 | 49 | |
| | | | 60 | 65 | At 180 min = 9 |
| | | | 180 | 87 | |

As seen from Table 1, the dependence of drug release rate (using a 0.1 N hydrochloric acid at pH 1.2) on tablet hardness increases with decreasing HPMC (METHOCEL® K100L V PREM CR) weight percentage in the extended layer mix (Layer #2). Tablet hardness is determined using conventional hardness testers routinely employed in the pharmaceutical industry. The amount of microcrystalline cellulose binder does not have an appreciable effect on the drug release rate. (Table 2). Release rates represent the overall rate of release for the entire tablet. However, substantially all of the active in the immediate release layer is released within 15 minutes. Therefore, variability of release at 60 minutes is attributable to the controlled release layer containing HPMC.

TABLE 2

Effect of Microcrystalline cellulose on Drug release variability associated with tablet hardness.

| % HPMC (K100) & % MCC | Drug/Polymer Ratio | Hardness | Time (min) | % Drug Release (D.R.) | Difference in % D.R. |
|---|---|---|---|---|---|
| 10 & 2.85 | 8.6 | 13 | 15 | 68 | At 15 min = 19 |
| | | | 60 | 85 | |
| | | | 180 | 96 | At 60 min = 20 |
| | | 24 | 15 | 49 | |
| | | | 60 | 65 | At 180 min = 9 |
| | | | 180 | 87 | |

TABLE 2-continued

Effect of Microcrystalline cellulose on Drug release variability associated with tablet hardness.

| % HPMC (K100) & % MCC | Drug/Polymer Ratio | Hardness | Time (min) | % Drug Release (D.R.) | Difference in % D.R. |
|---|---|---|---|---|---|
| 10 & 6.67 | 8.2 | 15.7 | 15 | 68 | At 15 min = 19 |
|  |  |  | 60 | 83 |  |
|  |  |  | 180 | 94 | At 60 min = 22 |
|  |  | 25.7 | 15 | 49 |  |
|  |  |  | 60 | 61 | At 180 min = 15 |
|  |  |  | 180 | 79 |  |

HPMC is used in this formulation as a matrix forming polymer that forms a gel-like matrix when hydrated. Drug release will occur either through direct drug diffusion from the polymer or through matrix erosion. As the percentage of the polymer is decreased to achieve a desired drug release profile, the drug/HPMC ratio increases, resulting in a loose dispersion of polymer molecules (loose polymer matrix) and the creation of bigger gaps in the polymer matrix. Such loose dispersion of the polymer in the formula results in a drug release profile that is strongly dependent on tablet hardness. For a highly compressed (harder) tablet, the polymer is tightly packed and drug release is slower. At lower compression force (softer tablet), the polymer is loosely packed and drug release is faster. This might result in dose dumping in some cases or (in the case of a formula using 10% METHOCEL® K100 L V PREM CR) variability in drug release associated with tablet hardness.

Increasing the amount of the binder will not eliminate this problem since the binder would help in producing harder tablets but would not address the problem of loose dispersion of the polymer at low percentages when soft tablets are produced. Use of more METHOCEL® K100L V PREM CR would eliminate such problem, but would result in decreased drug release below what is desired.

We have discovered that the use of lower molecular weight HPMC (METHOCEL® K3 PREM L V) in combination with METHOCEL® K100 L V PREM CR does not influence drug release and at the same time reduces or eliminates drug release variability associated with tablet hardness (Table 3). METHOCEL® K3 PREM LV is believed to have a number average molecule weight under 10,000 and METHOCEL® K100 L V PREM CR is believed to have a number average molecular weight over 20,000.

As can be seen from Table 3 over a range of 10 SCU's, the drug release (determined using a 0.1 N hydrochloric acid at pH 1.2) does not change more than 4%. This shows that low molecular weight HPMC (METHOCEL® K3 PREM L V) did eliminate drug release variability's associated with tablet hardness. METHOCEL® K3 PREM L V is a low molecular weigh HPMC polymer that is not controlled release grade. We believe that METHOCEL® K3 PREM L V serves as a physical linker between the longer chains of the METHOCEL® K100 L V PREM CR polymer and fills the gaps once wetting and gel formation occurs. Such action would minimize the influence of tablet hardness on drug release profile since the loose dispersion of the METHOCEL® K100 L V PREM CR polymer that would result in gaps is being filled with METHOCEL® PREM L V small chains.

FIG. 1, represents a comparison of drug release variabilities as a function of tablet hardness at 60 minutes for several METHOCEL® K100 L V PREM CR formulations. As the HPMC percentage decreased, the drug release variability increased. The use of METHOCEL® K3 PREM L V eliminated such problem with minimal effect on drug release.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. A pharmaceutical tablet comprising:
    an extended release formulation, the extended release formulation including a pharmaceutically active ingredient in an amount of at least 70% by weight, from about 4% to about 8% of a hydroxypropyl methylcellulose having

TABLE 3

Use of METHOCEL ® K3 PREM LV and its effect on drug release variability associated with tablet hardness.

|  | Drug/Polymer Ratio | Hardness | Time (min) | % Drug Release (D.R.) | Difference in % D.R. |
|---|---|---|---|---|---|
| K100 (10%) | 8.6 | 13 | 15 | 68 | At 15 min = 19 |
|  |  |  | 60 | 85 |  |
|  |  |  | 180 | 96 | At 60 min = 20 |
|  |  | 24 | 15 | 49 |  |
|  |  |  | 60 | 65 | At 180 min = 9 |
|  |  |  | 180 | 87 |  |
| K100 (9%) + K3 (6%) | 9.0 | 18.7 | 15 | 51 | At 15 min = 4 |
|  |  |  | 60 | 64 |  |
|  |  |  | 180 | 83 | At 60 min = 4 |
|  |  | 28.4 | 15 | 47 |  |
|  |  |  | 60 | 60 | At 180 min = 2 |
|  |  |  | 180 | 81 |  | a number average molecular weight of less than 10,000 Daltons, and from about 1% to about 10% of a hydroxypropyl methylcellulose having a number average molecular weight greater than 20,000 Daltons.

2. The extended release tablet of claim 1, wherein the active ingredient is an analgesic.

3. The extended release tablet of claim 1, wherein the active ingredient is acetaminophen.

4. The tablet of claim 1, wherein the extended release formulation is in an extended release portion of a tablet further comprising an immediate release portion containing a pharmaceutically active ingredient, which is the same or different from the pharmaceutically active ingredient in the extended release portion, and at least one disintegrant.

5. The tablet of claim 4, wherein the active ingredient in the extended release portion is an analgesic.

6. The tablet of claim 4, wherein the active ingredient in the extended release portion is acetaminophen.

* * * * *